(12) United States Patent
Kasaba et al.

(10) Patent No.: US 11,679,202 B2
(45) Date of Patent: Jun. 20, 2023

(54) INJECTOR CAPABLE OF SUPPRESSING SUBSEQUENT DRIPPING OF FLUID

(71) Applicant: KABUSHIKI KAISHA SHOFU, Kyoto (JP)

(72) Inventors: Hideto Kasaba, Kyoto (JP); Hiroyuki Kobayashi, Kyoto (JP); Hiroyuki Shioi, Kyoto (JP); Hiroshi Yaana, Kyoto (JP); Toshiyuki Nakatsuka, Kyoto (JP); Yukihiro Ogawa, Ibaraki (JP); Hisako Tokura, Ibaraki (JP)

(73) Assignee: KABUSHIKI KAISHA SHOFU, Kyoto (JP)

( * ) Notice: Subject to any disclaimer, the term of this patent is extended or adjusted under 35 U.S.C. 154(b) by 154 days.

(21) Appl. No.: 16/447,227

(22) Filed: Jun. 20, 2019

(65) Prior Publication Data

US 2019/0388620 A1    Dec. 26, 2019

(30) Foreign Application Priority Data

Jun. 21, 2018    (JP) .............................. JP2018-118257

(51) Int. Cl.
*A61M 5/31* (2006.01)
*A61M 5/315* (2006.01)

(52) U.S. Cl.
CPC ...... *A61M 5/3129* (2013.01); *A61M 5/31513* (2013.01); *A61M 2005/3103* (2013.01); *A61M 2005/3131* (2013.01)

(58) Field of Classification Search
CPC ............ A61M 5/3129; A61M 5/31513; A61M 2005/3103; A61M 2005/3131;
(Continued)

(56) References Cited

U.S. PATENT DOCUMENTS 3,809,082 A * 5/1974 Hurschman ....... A61M 5/31513
604/218
4,391,272 A 7/1983 Staempfli
(Continued)

FOREIGN PATENT DOCUMENTS

EP    1849490 A1 * 10/2007 ........ A61M 5/31515
JP    62-22634    5/1987
(Continued)

OTHER PUBLICATIONS

"Flange, 2011, Houghton Mifflin Harcourt Publishing Company, American Heritage® Dictionary of the English Language, Fifth Edition" (Year: 2011).*
(Continued)

*Primary Examiner* — Laura A Bouchelle
(74) *Attorney, Agent, or Firm* — Wenderoth, Lind & Ponack, L.L.P.

(57) ABSTRACT

An injector comprises a cylindrical barrel, a movable body housed in the barrel, and a plunger coming into separable contact with the movable body. The movable body includes a main body having an outer diameter smaller than an inner diameter of the barrel, a disk-shaped seal body disposed on the main body and including an outer circumferential end brought into close contact with an inner circumferential surface of the barrel, and at least one projecting portion projecting from the main body toward the inner circumferential surface of the barrel. A distance from a central axis of the movable body to a leading end of the at least one projecting portion is smaller than a half of an outer diameter of the seal body.

3 Claims, 14 Drawing Sheets

(58) Field of Classification Search
CPC ........... A61M 2005/3112; A61M 2005/31521; A61M 2005/31508; A61M 5/3135; A61M 2005/3139; A61M 2005/31506; A61M 5/31511; A61M 2005/3104; F04B 53/143; F04B 53/14; F04B 53/16; F04B 53/00; A61B 5/150236; A61J 7/0053

See application file for complete search history.

(56) References Cited

U.S. PATENT DOCUMENTS

| | | | | |
|---|---|---|---|---|
| 5,620,423 | A * | 4/1997 | Eykmann | A61C 5/62 604/218 |
| 6,224,577 | B1 | 5/2001 | Dedola et al. | |
| 6,796,217 | B2 * | 9/2004 | Horita | A61M 5/31511 92/240 |
| 9,199,043 | B2 * | 12/2015 | Chattaraj | A61M 5/31511 |
| 9,289,557 | B2 * | 3/2016 | Ivosevic | A61M 5/31513 |
| 2003/0035744 | A1 | 2/2003 | Horita et al. | |
| 2006/0173411 | A1 * | 8/2006 | Barere | A61M 5/5013 604/110 |
| 2011/0034882 | A1 * | 2/2011 | Quinn | A61M 5/31513 604/218 |
| 2012/0253291 | A1 | 10/2012 | Ivosevic et al. | |
| 2014/0031749 | A1 | 1/2014 | Chattaraj et al. | |
| 2014/0339776 | A1 * | 11/2014 | Nakano | A61M 5/31513 277/358 |

FOREIGN PATENT DOCUMENTS

| | | |
|---|---|---|
| JP | 2703592 | 1/1998 |
| JP | 3095200 | 10/2000 |
| JP | 2003-135487 | 5/2003 |
| JP | 4014115 | 11/2007 |
| JP | 4434342 | 3/2010 |
| JP | 2015-517860 | 6/2015 |
| JP | 2015-160636 | 9/2015 |
| WO | 89/06146 | 7/1989 |
| WO | 98/28030 | 7/1998 |
| WO | 2013/178771 | 12/2013 |
| WO | 2018/083221 | 5/2018 |
| WO | WO-2018083221 A * | 5/2018 ........ A61M 5/31513 |

OTHER PUBLICATIONS

Extended European Search Report dated Sep. 12, 2019 in European Patent Application No. 19181133.0.

Communication pursuant to Article 94(3) EPC dated Feb. 2, 2022 in corresponding EP Application No. 19 181 133.0.

Chinese Office Action dated Dec. 2, 2021 in corresponding Chinese Patent Application No. 201910536167.2 with English machine translation.

Japanese Office Action dated Dec. 14, 2021 in corresponding Japanese Patent Application No. 2018-118257 with English machine translation.

Office Action dated Jun. 8, 2022 in corresponding Chinese Patent Application No. 201910536167.2.

Office Action dated Nov. 1, 2022 in corresponding Chinese Patent Application No. 201910536167.2, with Machine Translation, 12 pages.

Decision of Refusal dated Jul. 5, 2022 in corresponding Japanese Patent Application No. 2018-118257, with English language translation.

* cited by examiner

INJECTOR CAPABLE OF SUPPRESSING SUBSEQUENT DRIPPING OF FLUID

TECHNICAL FIELD

The present invention relates to an injector.

BACKGROUND ART

An injector for injecting a fluid is conventionally known. For example, the injector described in Patent Document 1 is configured such that after pushing out a necessary amount of fluid through a discharge port to the outside of a barrel, the fluid remaining inside the barrel does not leak automatically through the discharge port, i.e., "subsequent dripping" of the fluid does not occur.

Specifically, in the case of the injector described in Patent Document 1, a disk-shaped seal body is integrally disposed at a front end of a plunger. An outer circumferential end of the seal body is in close contact with an inner circumferential surface of the barrel.

When the plunger advances toward the discharge port of the barrel, the disk-shaped seal body pushes and moves the fluid toward the discharge port while elastically deforms into a closed umbrella shape. When the plunger stops, the seal body returns from the closed umbrella shape to the disk shape. In this case, a central portion of the seal body is shifted in a direction away from the discharge port without changing a position of the inner circumferential surface of the barrel at which the outer circumferential end of the seal body is in contact. As a result, the fluid is drawn toward the seal body, and the subsequent dripping of the fluid is suppressed.

PRIOR ART DOCUMENT

Patent Document

Patent Document 1: Japanese Laid-Open Patent Publication No. 2003-135487

SUMMARY OF THE INVENTION

Problem to be Solved by the Invention

To prevent the seal body in close contact with the inner circumferential surface of the barrel from coming off to the outside of the barrel, an injector having the seal body and the plunger coming into separable contact with each other is required. This allows the seal body to remain in the barrel without retracting even if the plunger is retracted. As a result, air is prevented from entering the fluid in the barrel from the base end side of the barrel. This also prevents air from entering from the discharge port due to retracting of the seal body.

Therefore, a problem to be solved by the present invention is to bring a seal body and a plunger into separable contact with each other in an injector capable of suppressing subsequent dripping of a fluid.

Means for Solving Problem

To solve the problem described above, an aspect of the present disclosure provides
an injector comprising:
a cylindrical barrel;
a movable body housed in the barrel; and
a plunger coming into separable contact with the movable body, wherein
the movable body includes
a main body having an outer diameter smaller than an inner diameter of the barrel,
a disk-shaped seal body disposed on the main body and including an outer circumferential end brought into close contact with an inner circumferential surface of the barrel, and
at least one projecting portion projecting from the main body toward the inner circumferential surface of the barrel, and wherein
a distance from a central axis of the movable body to a leading end of the at least one projecting portion is smaller than a half of an outer diameter of the seal body.

Effect of the Invention

According to the present invention, the seal body and the plunger can be brought into separable contact with each other in the injector capable of suppressing subsequent dripping of a fluid.

MODES FOR CARRYING OUT THE INVENTION

An injector according to an embodiment of the present invention comprises a cylindrical barrel, a movable body housed in the barrel, and a plunger coming into separable contact with the movable body; the movable body includes a main body having an outer diameter smaller than an inner diameter of the barrel, a disk-shaped seal body disposed on the main body and including an outer circumferential end brought into close contact with an inner circumferential surface of the barrel, and at least one projecting portion projecting from the main body toward the inner circumferential surface of the barrel; and a distance from a central axis of the movable body to a leading end of the at least one projecting portion is smaller than a half of an outer diameter of the seal body.

According to this aspect, the seal body and the plunger can be brought into separable contact with each other in the injector capable of suppressing subsequent dripping of a fluid.

The at least one projecting portion may be a flange. In this case, an outer diameter of the flange is made smaller than the outer diameter of the seal body.

The outer diameter of the flange may be smaller than the inner diameter of the barrel. As a result, the flange can be moved without strong contact with the inner circumferential surface of the barrel, i.e., in a state of substantially zero friction force.

A distance between the seal body and the flange may be larger than the outer diameter of the seal body. As a result, the movable body is restrained from tilting.

The plunger may include a planar-shaped contact surface at a front end thereof, and the movable body may include a planar-shaped rear end surface coming into contact with the contact surface of the plunger. As a result, the movable body can be pushed and moved by the plunger without tilting.

The plunger may include a guide pin projecting from the contact surface, and the movable body may include in the rear end surface a guide hole receiving the guide pin in a manner enabling forward and backward movement. Since the guide pin is guided by the guide hole, the rear end surface of the movable body and the contact surface of the plunger can appropriately contact with each other.

Embodiments of the present invention will now be described with reference to the drawings.

First Embodiment

Figure 1:
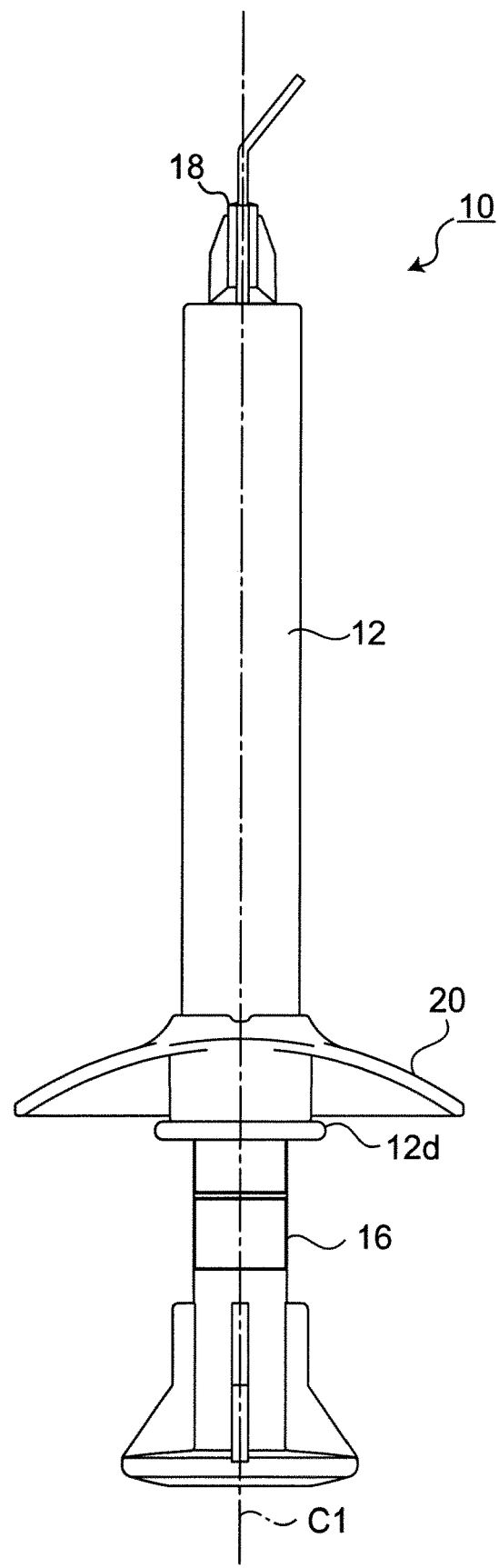
FIG. 1 is an external view of an injector according to a first embodiment of the present invention.
Figure 2:
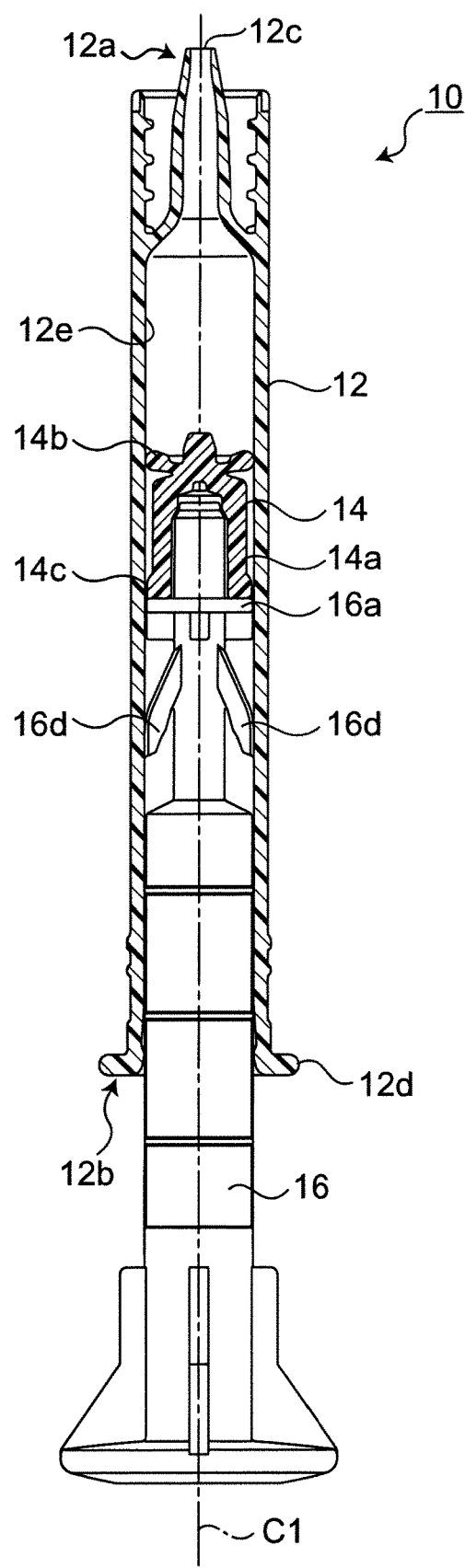
FIG. 2 is a partial cross-sectional view of the injector according to the first embodiment.

FIG. 1 is an external view of an injector according to a first embodiment of the present invention, and FIG. 2 is a partial cross-sectional view of the injector.

As shown in FIGS. 1 and 2, an injector 10 includes a barrel 12 containing, for example, a pasty fluid, a movable body 14 movably housed in the barrel 12, and a plunger 16 for pushing and moving the movable body 14. The injector 10 also has a nozzle tip 18 attached to a leading end 12a of the barrel 12 and a finger grip 20 rotatably fitted to a base end 12b of the barrel 12.

Figure 3:
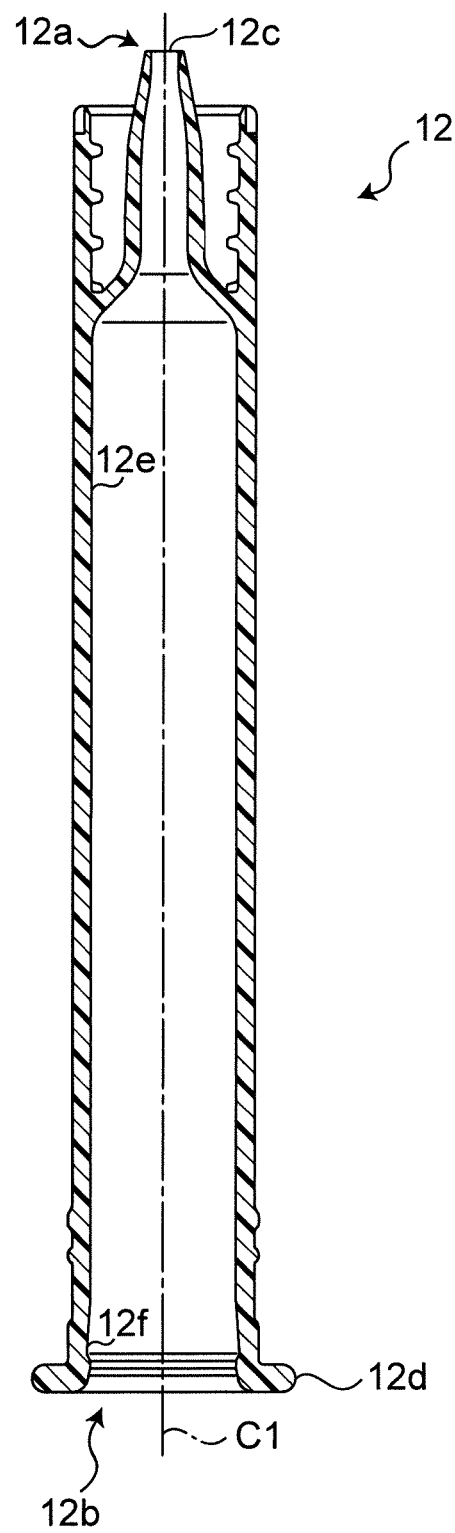
FIG. 3 is a cross-sectional view of a barrel in the injector according to the first embodiment.
Figure 4:
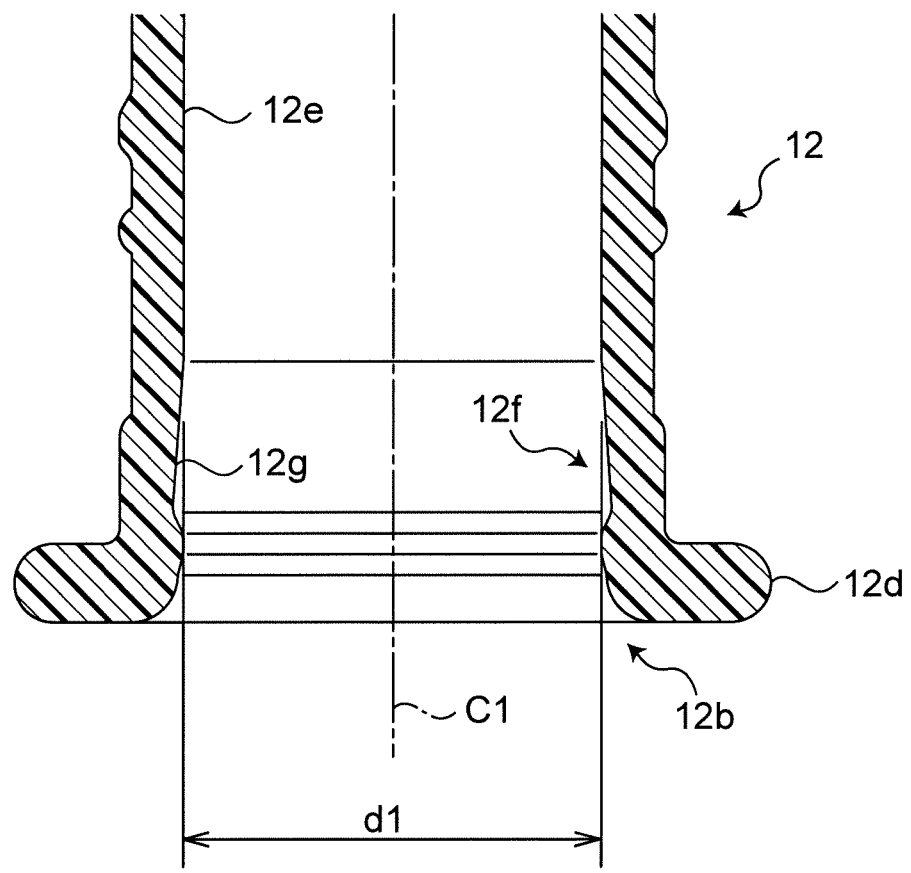
FIG. 4 is an enlarged cross-sectional view of the barrel shown in FIG. 3.

FIG. 3 is a cross-sectional view of the barrel, and FIG. 4 is an enlarged cross-sectional view of the barrel shown in FIG. 3.

As shown in FIG. 3, the barrel 12 is a cylindrical member having a central axis C1, and is made of a resin material, for example. The barrel 12 includes a discharge port 12c at the leading end 12a and a flange portion 12d at the base end 12b. By attaching the nozzle tip 18 to the leading end 12a of the barrel 12, the discharge port 12c is connected to a nozzle inside flow passage communicating with the outside in the nozzle tip 18. The flange portion 12d functions as a stopper preventing the finger grip 20 rotatably fitted to a base end side portion of the barrel 12 from falling off.

As shown in FIG. 4, a circumferential groove 12f is formed in a base end side portion of an inner circumferential surface 12e of the barrel 12. The reason why the circumferential groove 12f is formed will be described later.

Figure 5:
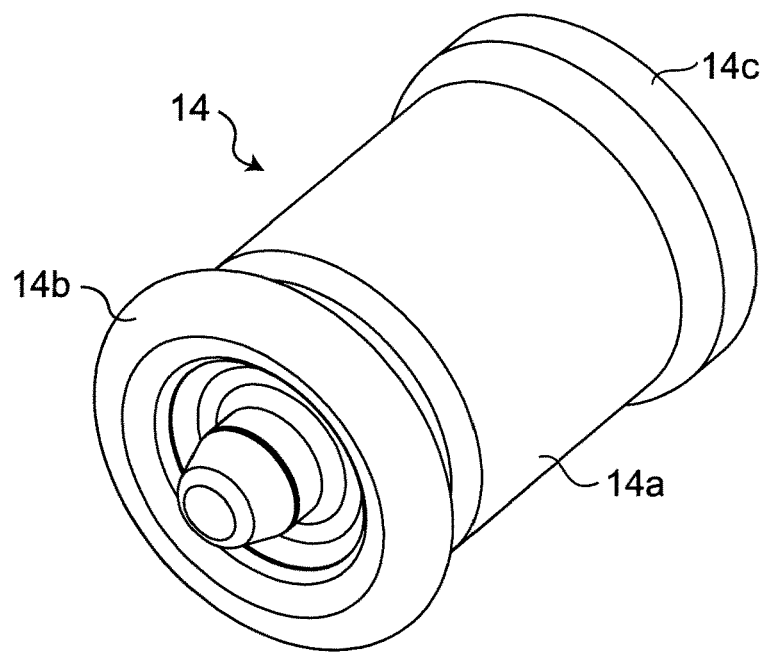
FIG. 5 is a perspective view of a movable body in the injector according to the first embodiment.
Figure 6:
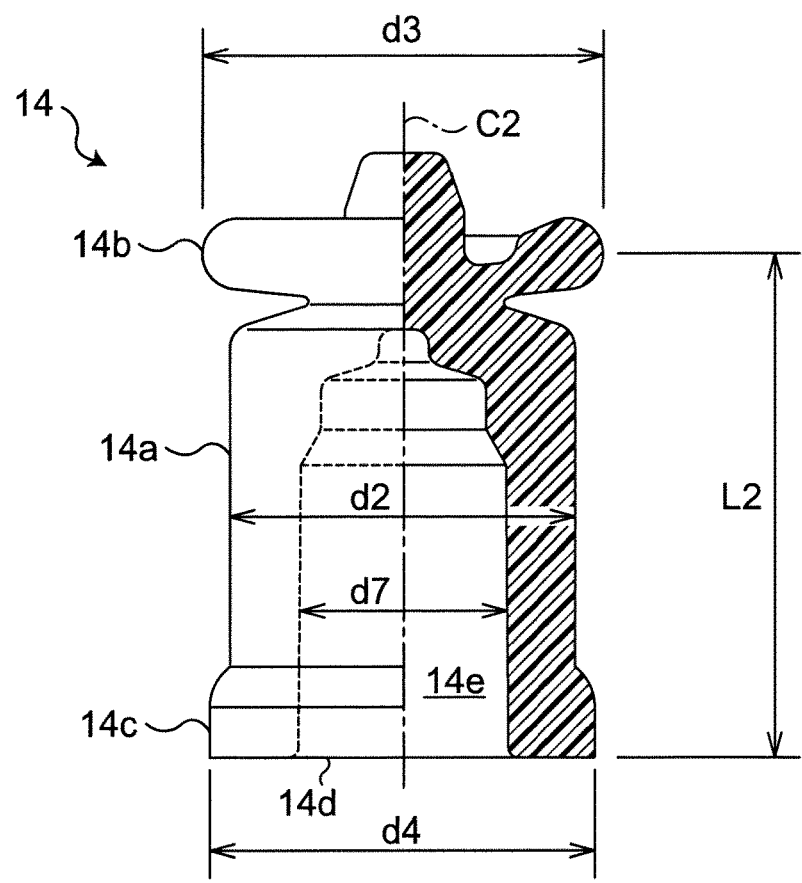
FIG. 6 is a partial cross-sectional view of the movable body shown in FIG. 5.

FIG. 5 is a perspective view of the movable body, and FIG. 6 is a partial cross-sectional view of the movable body.

As shown in FIG. 5, the movable body 14 is a substantially cylindrical member having a central axis C2. The movable body 14 is made of an elastically deformable resin material, for example. Specifically, the movable body 14 is made of a material easily elastically deformed as compared to the barrel 12.

The movable body 14 includes a main body 14a, a seal body 14b disposed on the main body 14a, and a flange 14c disposed on the main body 14a.

The main body 14a of the movable body 14 is cylindrical and has an outer diameter d2 smaller than an inner diameter d1 of the barrel 12 shown in FIG. 4. Therefore, while the movable body 14 is housed in the barrel 12, a clearance is generated between the main body 14a and the inner circumferential surface 12e of the barrel 12.

The seal body 14b of the movable body 14 has a disk shape and has an outer circumferential end brought into close contact with the inner circumferential surface 12e of the barrel 12 in a slidable and fluid-tight manner. Although the seal body 14b and the main body 14a are integrated as one part, the seal body 14b and the main body 14a may be separate parts.

For close contact of the outer circumferential end with the inner circumferential surface 12e of the barrel 12 in a fluid-tight manner, the seal body 14b has an outer diameter d3 larger than the inner diameter d1 of the barrel 12. The outer diameter d3 of the seal body 14b is larger than the outer diameter d2 of the main body 14a of the movable body 14.

Additionally, the seal body 14b has a central portion attached to a front end of the main body 14a (the end closer to the leading end 12a of the barrel 12). Additionally, an outer circumferential side portion of the seal body 14b is away from the main body 14a when the portion is in a free state (when the movable body 14 is present outside the barrel 12).

The flange 14c of the movable body 14 is a projecting portion projecting from the main body toward the inner circumferential surface of the barrel 12 and is disposed at a rear end of the main body 14a (the end closer to the base end 12b of the barrel 12). The flange 14c has an outer diameter d4 smaller than the outer diameter d3 of the seal body 14b. In the case of the first embodiment, the outer diameter d4 of the flange 14c is smaller than the inner diameter d1 of the barrel 12 and larger than the outer diameter d2 of the main body 14a. The reason why the flange 14c as described above is disposed on the movable body 14 will be described later.

For separable contact with the plunger 16, the movable body 14 also includes a planar-shaped rear end surface 14d orthogonal to the central axis C2 and includes a non-penetrating hole-shaped guide hole 14e in the rear end surface 14d.

Figure 7:
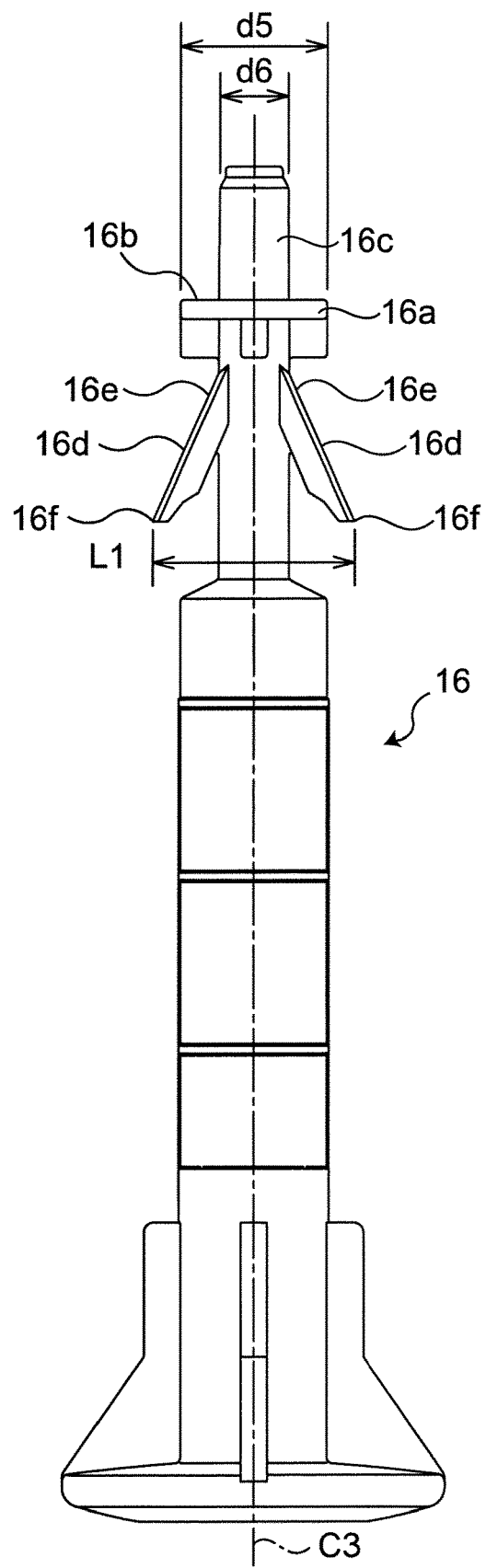
FIG. 7 is an external view of a plunger in the injector according to the first embodiment.

FIG. 7 is an external view of the plunger.

As shown in FIG. 7, the plunger 16 is a member for pushing and moving the movable body 14 housed in the barrel 12 toward the leading end 12a (i.e., the discharge port 12c) of the barrel 12, has a central axis C3, and is made of a resin material, for example. The plunger 16 is configured to come into separable contact with the movable body 14.

Specifically, the plunger 16 includes a contact portion 16a coming into contact with the movable body 14 on the front end side (the side closer to the leading end 12a of the barrel 12). The contact portion 16a has an outer diameter d5 smaller than the inner diameter d1 of the barrel 12. The contact portion 16a includes a planar-shaped contact surface 16b coming into surface contact with the planar-shaped rear end surface 14d of the movable body 14.

The plunger 16 includes a guide pin 16c projecting from the contact surface 16b of the contact portion 16a. While the rear end surface 14d of the movable body 14 is in surface contact with the contact surface 16b of the plunger 16, the guide pin 16c is received in the guide hole 14e of the movable body 14. An outer diameter d6 of the guide pin 16c is smaller than an inner diameter d7 of the guide hole 14e shown in FIG. 6 so that the guide pin is received in the guide hole 14e of the movable body 14 in a manner enabling forward and backward movement. Since the guide pin 16c is guided by the guide hole 14e, the contact surface 16b of the plunger 16 can appropriately come into surface contact with the rear end surface 14d of the movable body 14. Specifically, the movable body 14 and the plunger 16 can come into contact with each other in a state in which the central axis C2 of the movable body 14 and the central axis C3 of the plunger 16 are arranged substantially on the same straight line. As a result, the plunger 16 can push and move the movable body 14 toward the leading end 12a of the barrel 12 without tilting.

According to the plunger 16 as described above, the movable body 14 can be pushed and moved toward the leading end 12a of the barrel 12 by advancing the plunger 16. Additionally, the movable body 14 and the plunger 16 can be separated from each other by simply retracting the plunger 16.

Since the plunger 16 is not fixed to the movable body 14 while the seal body 14b is in close contact with the inner circumferential surface 12e of the barrel 12, the plunger 16 possibly comes off from the barrel 12. For example, if the injector 10 is in a state with the nozzle tip 18 located downward and a user grasps only the plunger 16 to lift the injector 10, the barrel 12 may fall off from the plunger 16 due to its own weight.

To prevent the plunger 16 from coming off from the barrel 12 in this way, stoppers 16d are disposed on the plunger 16 as shown in FIG. 7.

In the case of the first embodiment, the two stoppers 16d are disposed oppositely to each other across the central axis C3 of the plunger 16. Each of the two stoppers 16d is an elastically-deformable plate spring-shaped member including a fixed end 16e attached to the plunger 16 and a free end 16f displaceable in a radial direction of the barrel 12 (a direction orthogonal to the central axis C1 of the barrel 12). In the case of the first embodiment, the stoppers 16d and the plunger 16 are integrated as one part.

In the case of the first embodiment, the free end 16f of the stopper 16d is located on the base end 12b side of the barrel 12 with respect to the fixed end 16e. The free end 16f is farther than the fixed end 16e from the central axis C3 of the plunger 16. Therefore, the stopper 16d extends from the leading end 12a side to the base end 12b side of the barrel 12 and toward the inner circumferential surface 12e of the barrel 12.

As shown in FIG. 7, a distance L1 between the free ends 16f of the two stoppers 16d is larger than the inner diameter d1 of the barrel 12 when the free ends are in a free state (when the plunger 16 is present outside the barrel 12). Therefore, when the stoppers 16d of the plunger 16 are located inside the barrel 12, each of the two stoppers 16d is elastically deformed by the inner circumferential surface 12e of the barrel 12 such that the free ends 16f come closer to each other. This brings the free ends 16f of the stopper 16d into elastic contact with the inner circumferential surface 12e of the barrel 12 in the radial direction of the barrel 12. As a result, a friction force is generated between the barrel 12 and the free ends 16f of the stopper 16d, and the plunger 16 is restrained from coming off from the barrel 12. The term "elastic contact" as used herein means that a portion of an object during elastic deformation is in contact with another object in a restoring direction in which the object is restored to an original shape.

An elastic force of the stoppers 16d, i.e., the friction force between the inner circumferential surface 12e of the barrel 12 and the free ends 16f of the stoppers 16d, is at a level preventing the barrel 12 from coming off when a user grasps only the plunger 16 of the injector 10 in a posture with the nozzle tip 18 located downward, or at a level preventing the plunger 16 from coming off when a user grasps only the barrel 12 of the injector 10 in a posture with the nozzle tip 18 located upward. Additionally, this elastic force (i.e., friction force) is at a level allowing the user to push and move the plunger 16 toward the leading end 12a of the barrel 12. To achieve such an elastic force (i.e., friction force), the materials of the barrel 12 and the stoppers 16d, the shape of the stoppers 16d, etc. are appropriately selected.

According to the stoppers 16d as described above, the plunger 16 can be prevented from coming off from the barrel 12 without disposing a convex portion on the inner circumferential surface 12e of the barrel 12. Therefore, when the movable body 14 is housed into the barrel 12, the seal body 14b is not damaged by the convex portion disposed on the inner circumferential surface 12e.

According to the stoppers 16d as described above, the plunger 16 can be anchored at an arbitrary position on the inner circumferential surface 12e of the barrel 12. As a result, the injector 10 can have high usability.

Furthermore, in the case of the first embodiment, the two stoppers 16d are arranged oppositely to each other across the central axis C3 of the plunger 16, so that the central axis C3 of the plunger 16 can be aligned with the central axis C1 of the barrel 12.

Although the free ends 16f of the stoppers 16d are in elastic contact with the inner circumferential surface 12e of the barrel 12, if the user moves the plunger 16 backward, the free end 16f slides on the inner circumferential surface 12e, and the plunger 16 finally comes off from the barrel 12. To deal with such coming-off due to the user, as shown in FIG. 4, the circumferential groove 12f is formed in a portion near the base end 12b in the inner circumferential surface 12e of the barrel 12. The free ends 16f of the stoppers 16d engage with (fall and fit into) the circumferential groove 12f, so that the plunger 16 is restricted from moving toward the base end side of the barrel 12, and as a result, the plunger 16 is prevented from coming off from the barrel 12.

When the plunger 16 is housed into the barrel 12, the free ends 16f of the stoppers 16d may be caught in the circumferential groove 12f, which possibly makes it unable to smoothly move the plunger 16 toward the leading end 12a of the barrel 12. As a countermeasure, as shown in FIG. 4, the circumferential groove 12f includes a slope surface 12g extending from a bottom portion thereof toward the leading end 12a of the barrel 12 and sloping with respect to the inner circumferential surface 12e. Due to the slope surface 12g, the free end 16f falling into the circumferential groove 12f can return onto the inner circumferential surface 12e. As a result, the free ends 16f of the stoppers 16d can pass through the circumferential groove 12f without being caught.

When the movable body 14 is housed into the barrel 12, the slope surface 12g can also prevent the seal body 14b of the movable body 14 from being caught in the circumferential groove 12f. As a result, the seal body 14b can be prevented from being damaged by the circumferential groove 12f.

While describing the operation of the injector 10 according to the first embodiment, other features of the injector 10 will hereinafter be described with reference to FIGS. 8A to 8D.

Figure 8A:
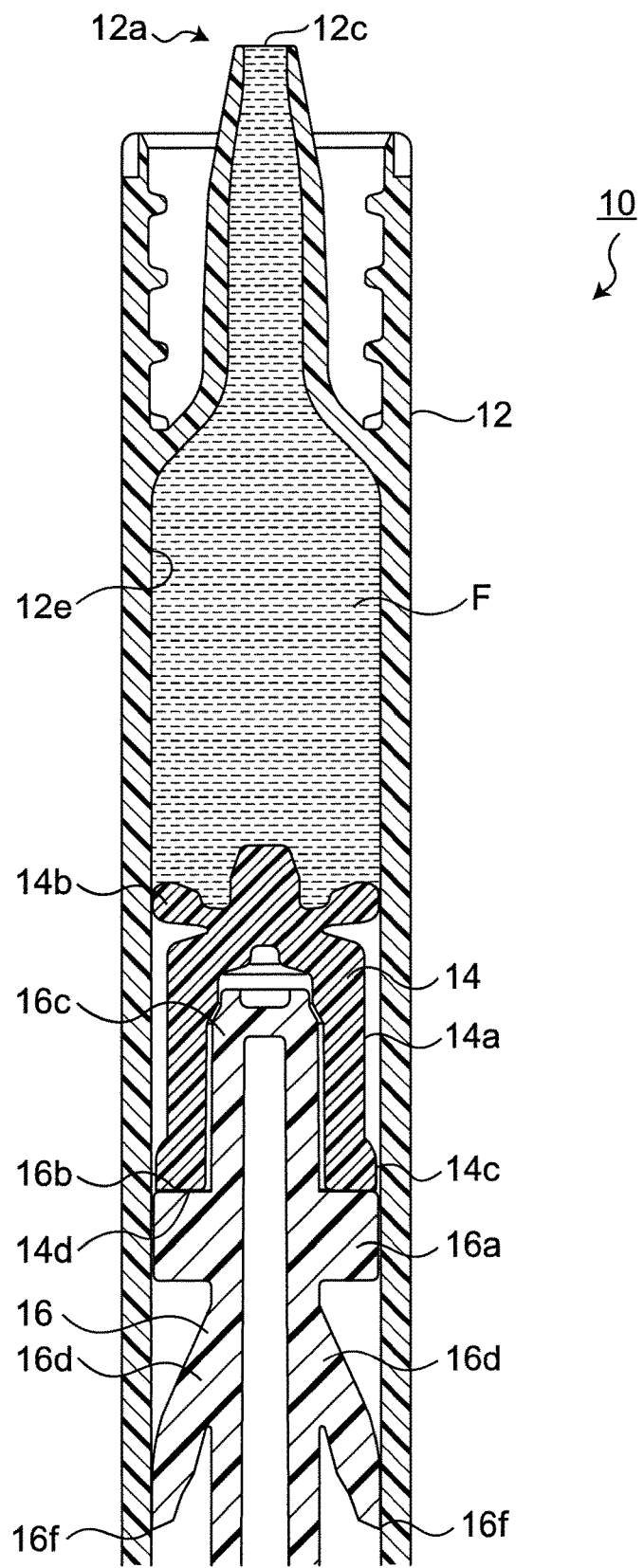
FIG. 8A is an enlarged cross-sectional view of the barrel while the plunger and the movable body are stopped.

FIG. 8A is an enlarged cross-sectional view of the barrel while the plunger and the movable body are stopped.

As shown in FIG. 8A, the seal body 14b of the movable body 14 is in close fluid-tight contact with the inner circumferential surface 12e of the barrel 12, so that a fluid F is contained in the barrel 12 without leaking from the base end side of the barrel 12 to the outside.

Figure 8B:
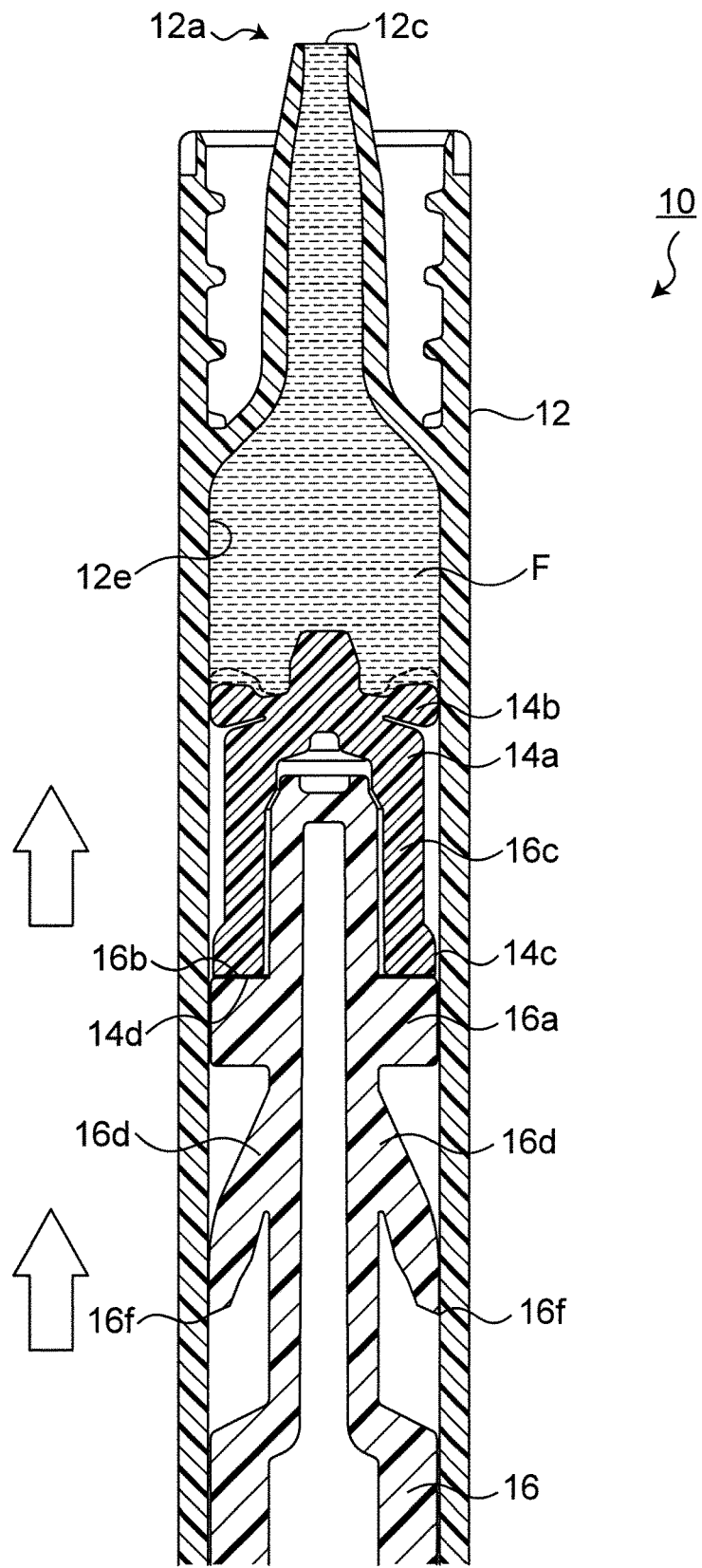
FIG. 8B is an enlarged cross-sectional view of the barrel during movement of the plunger and the movable body toward a leading end of the barrel.

FIG. 8B is an enlarged cross-sectional view of the barrel during movement of the plunger and the movable body toward the leading end of the barrel.

As shown in FIG. 8B, while the rear end surface 14d of the movable body 14 and the contact surface 16b of the plunger 16 are in contact with each other, the movable body 14 is pushed and moved toward the leading end 12a of the barrel 12 by the plunger 16. During movement of the movable body 14, the seal body 14b is elastically deformed. Specifically, due to the friction force generated between the outer circumferential end of the seal body 14b and the inner circumferential surface 12e of the barrel 12, the seal body 14b is elastically deformed such that the outer circumferential side portion of the seal body 14b approaches the main body 14a. The seal body 14b moves in this elastically deformed state and pushes and moves the fluid F toward the discharge port 12c.

Figure 8C:
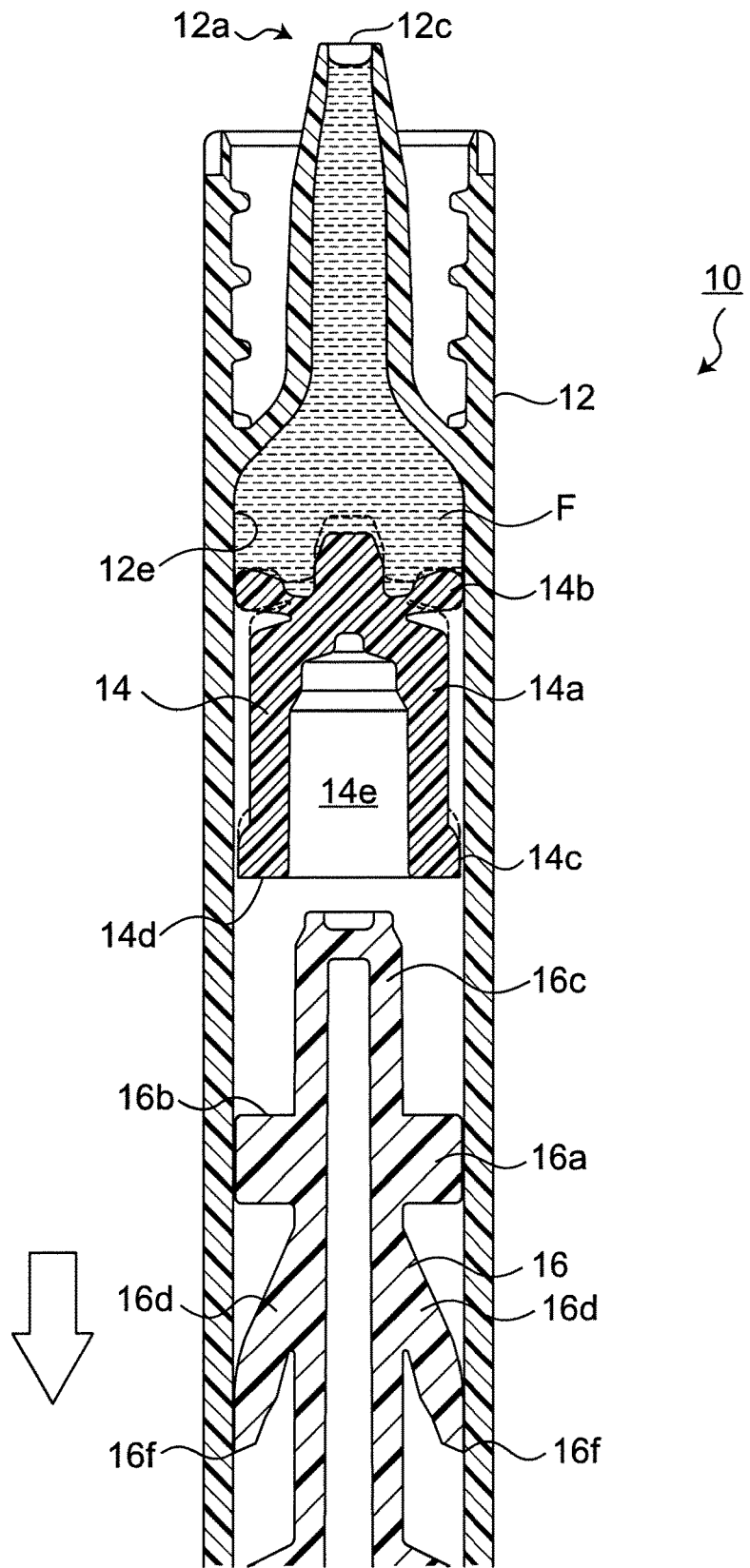
FIG. 8C is an enlarged cross-sectional view of the barrel during movement of the plunger in a direction away from the movable body.

FIG. 8C is an enlarged cross-sectional view of the barrel during movement of the plunger in a direction away from the movable body.

As shown in FIG. 8C, when the plunger 16 moves in a direction away from the movable body 14, i.e., toward the base end of the barrel 12, the movable body 14 is separated from the plunger 16 and stops in the barrel 12 in this state.

Immediately after the movable body 14 stops, as shown in FIG. 8A, the seal body 14b is returned (restored) to the original shape with the outer circumferential side portion separated from the main body 14a. In this case, the movable body 14 entirely retracts toward the base end of the barrel 12 without changing the contact position on the inner circumferential surface 12e of the barrel 12 in contact with the outer circumferential end of the seal body 14b. As a result, the fluid F in the nozzle tip 18 is drawn toward the seal body 14b, and the subsequent dripping of the fluid F is suppressed.

To allow the movable body 14 to retract toward the base end of the barrel 12 through the restoration of the seal body 14b without changing the position of contact of the seal body 14b with the barrel 12, the plunger 16 needs to retreat at the same time. In other words, a restoring force of the seal body 14b needs to exceed the friction force between the free ends 16f of the stoppers 16d of the plunger 16 and the inner circumferential surface 12e of the barrel 12. For this purpose, the material of the seal body 14b, the shape of the seal body 14b, etc. are appropriately selected.

When the movable body 14 retracts through the restoration of the seal body 14b without changing the position of contact of the seal body 14b with the barrel 12 as described above, the flange 14c is moved along the inner circumferential surface 12e of the barrel 12. As a result, the movable body 14 can retreat in the extending direction of the central axis C1 of the barrel 12. If the flange 14c does not exit, the movable body 14 retracts in a direction tilted with respect to the central axis C1 of the barrel 12, so that the movable body 14 may have a posture in which a portion of an outer edge of the rear end surface 14d comes into contact with the inner circumferential surface 12e of the barrel 12, i.e., a tilted posture. If the movable body 14 is tilted, the adhesion between the seal body 14b and the inner circumferential surface 12e of the barrel 12 is partially weakened, so that the fluid F may leak to the base end side of the barrel 12.

In the case of the first embodiment, the outer diameter d4 of the flange 14c of the movable body 14 is smaller than the inner diameter d1 of the barrel 12. Therefore, the flange 14c can be moved without strong contact with the inner circumferential surface 12e of the barrel 12, i.e., in a state of substantially zero friction force. Alternatively, the outer diameter d4 of the flange 14c of the movable body 14 may be equal to or larger than the inner diameter d1 of the barrel 12. However, the friction force between the flange 14c and the barrel 12 must be smaller than the friction force between the seal body 14b and the barrel 12. Otherwise, the restoration of the seal body 14b and the retraction of the movable body 14 due to the restoration cannot be achieved.

In the case of the first embodiment, as shown in FIG. 6, the distance L2 between the seal body 14b and the flange 14c in the movable body 14 is made larger than the outer diameter d3 of the seal body 14b. Therefore, when the movable body 14 retracts due to the restoration of the seal body 14b, the movable body 14 is hardly tilted (as compared to when the distance L2 is smaller than the outer diameter d3).

As shown in FIG. 8C, the plunger 16 separated from the movable body 14 is kept housed in the barrel 12 by the stoppers 16d without coming off from the barrel 12.

Figure 8D:
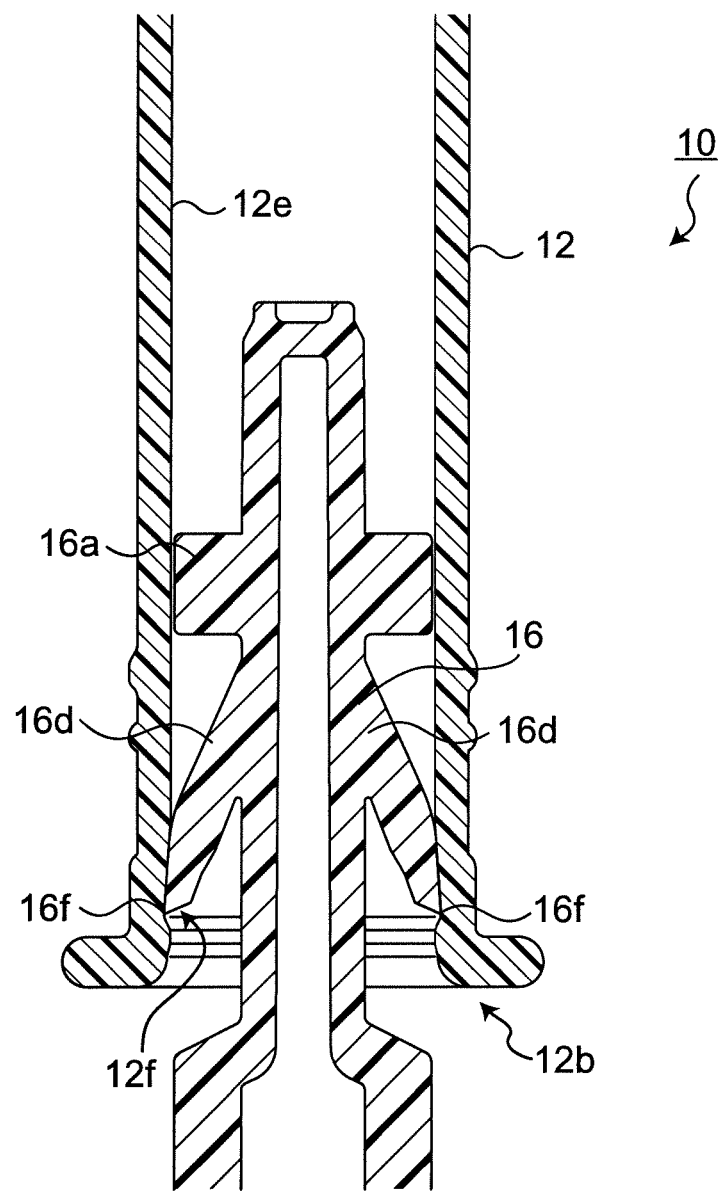
FIG. 8D is an enlarged cross-sectional view of the barrel while the plunger is restricted from coming off from the barrel by a circumferential groove.

FIG. 8D is a partially enlarged cross-sectional view of the barrel while the plunger is restricted from coming off from the barrel by the circumferential groove.

As shown in FIG. 8D, the plunger 16 during retraction toward the base end of the barrel 12 due to pulling by the user is restrained by engagement of the free ends 16f of the stoppers 16d with the circumferential groove 12f. As a result, the plunger 16 is prevented from coming off from the barrel 12.

According to the first embodiment as described above, the seal body and the plunger can be brought into separable contact with each other in the injector capable of suppressing the subsequent dripping of the fluid.

SECOND EMBODIMENT

A second embodiment is substantially the same as the first embodiment as described above except that the form of the stoppers disposed on the plunger is different. Therefore, the second embodiment will be described mainly in terms of different points. The same reference numerals are given to constituent elements in the second embodiment that are substantially the same as the constituent elements in the first embodiment described above.

Figure 9:
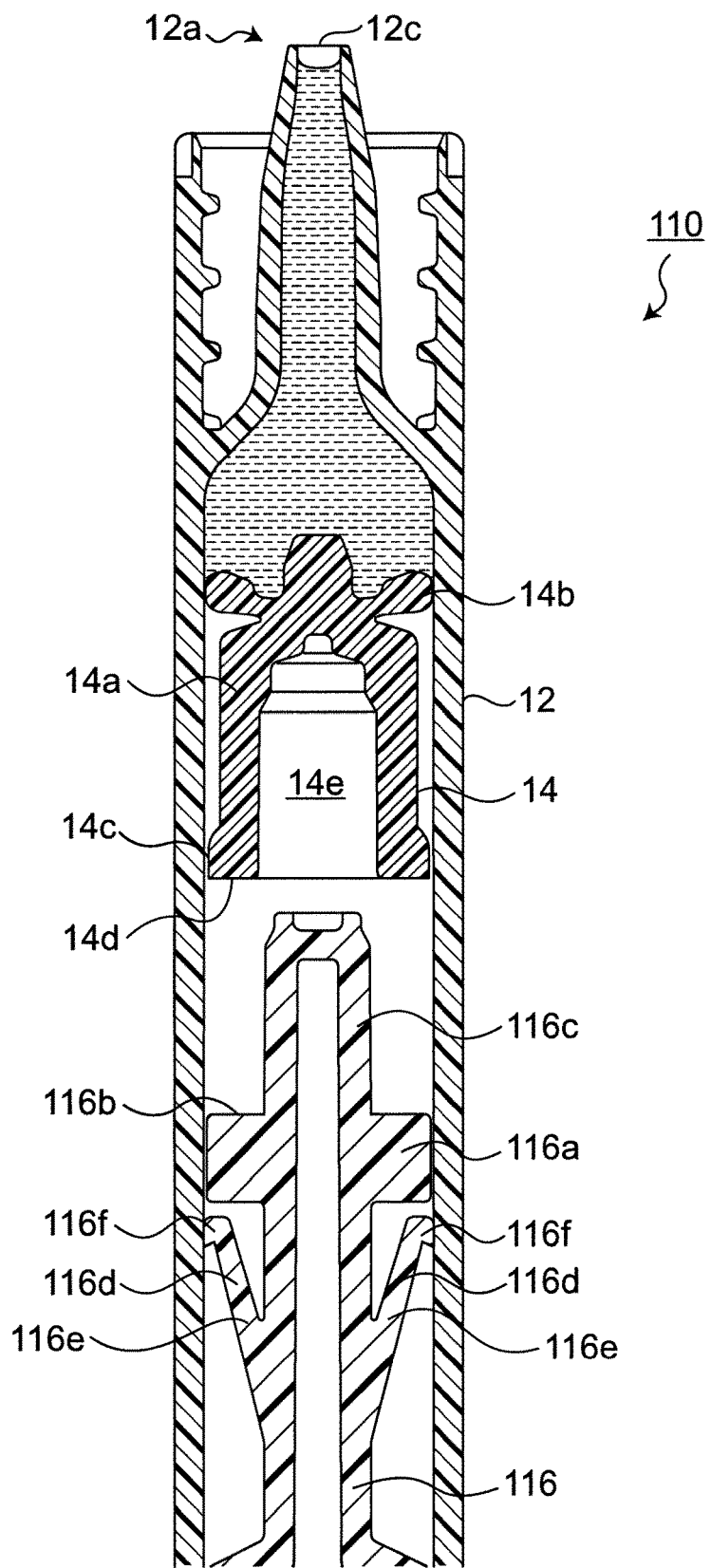
FIG. 9 is an enlarged cross-sectional view of a leading end portion of a barrel in an injector according to a second embodiment of the present invention.
Figure 10:
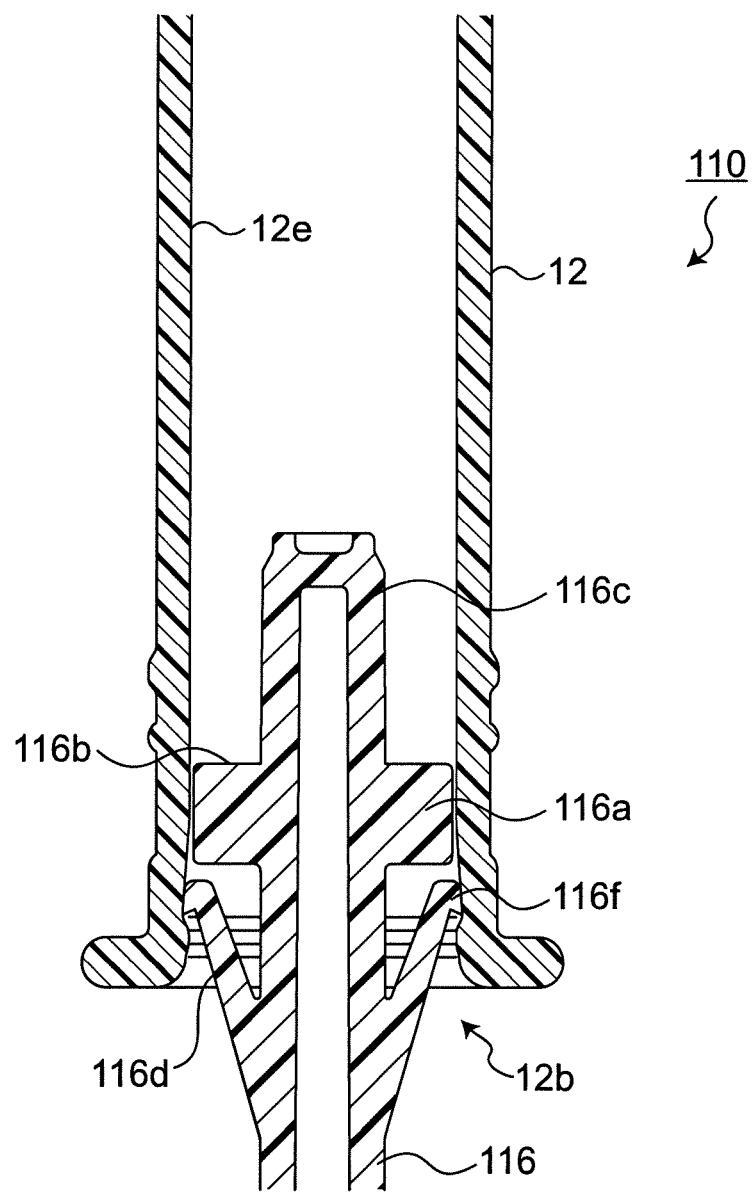
FIG. 10 is an enlarged cross-sectional view of a base end side portion of the barrel in the injector according to the second embodiment.

FIG. 9 is an enlarged cross-sectional view of a leading end side portion of a barrel in an injector according to the second embodiment. FIG. 10 is an enlarged cross-sectional view of a base end side portion of the barrel.

As shown in FIG. 9, in an injector 110 according to the second embodiment, a plunger 116 includes stoppers 116d. Each of the stoppers 116d is a plate spring-shaped member including a fixed end 116e attached to the plunger 116 and a free end 116*f* elastically contacting the inner circumferential surface 12*e* of the barrel 12.

In the case of the second embodiment, unlike the stopper 16*d* of the first embodiment, the free end 116*f* of the stopper 116*d* is located on the leading end side of the barrel 12 with respect to the fixed end 116*e*. Therefore, a contact surface 116*b* of the plunger 116 coming into contact with the rear end surface 14*d* of the movable body 14 is closer to the free end 116*f* of the stopper 116*d* as compared to the first embodiment shown in FIG. 8D.

Thus, as shown in FIG. 10, when the free end 116*f* of the stopper 116*d* is engaged with the circumferential groove of the barrel 12, the contact surface 116*b* of the plunger 116 is located closer to the base end 12*b* of the barrel 12. In other words, the movable body 14 having the rear end surface 14*d* brought into contact with the contact surface 116*b* is also disposed closer to the base end 12*b* of the barrel 12. As a result, a larger amount of the fluid can be contained in the barrel 12.

In the second embodiment as described above, as with the first embodiment, the seal body and the plunger can be brought into separable contact with each other in the injector capable of suppressing the subsequent dripping of the fluid.

Third Embodiment

In the case of the first embodiment described above, the stoppers preventing the plunger from coming off from the barrel are disposed on the plunger. In contrast, in the case of a third embodiment, stoppers are disposed on the barrel. Therefore, the third embodiment will be described mainly in terms of the different stoppers. The same reference numerals are given to constituent elements in the third embodiment that are substantially the same as the constituent elements in the first embodiment described above.

Figure 11:
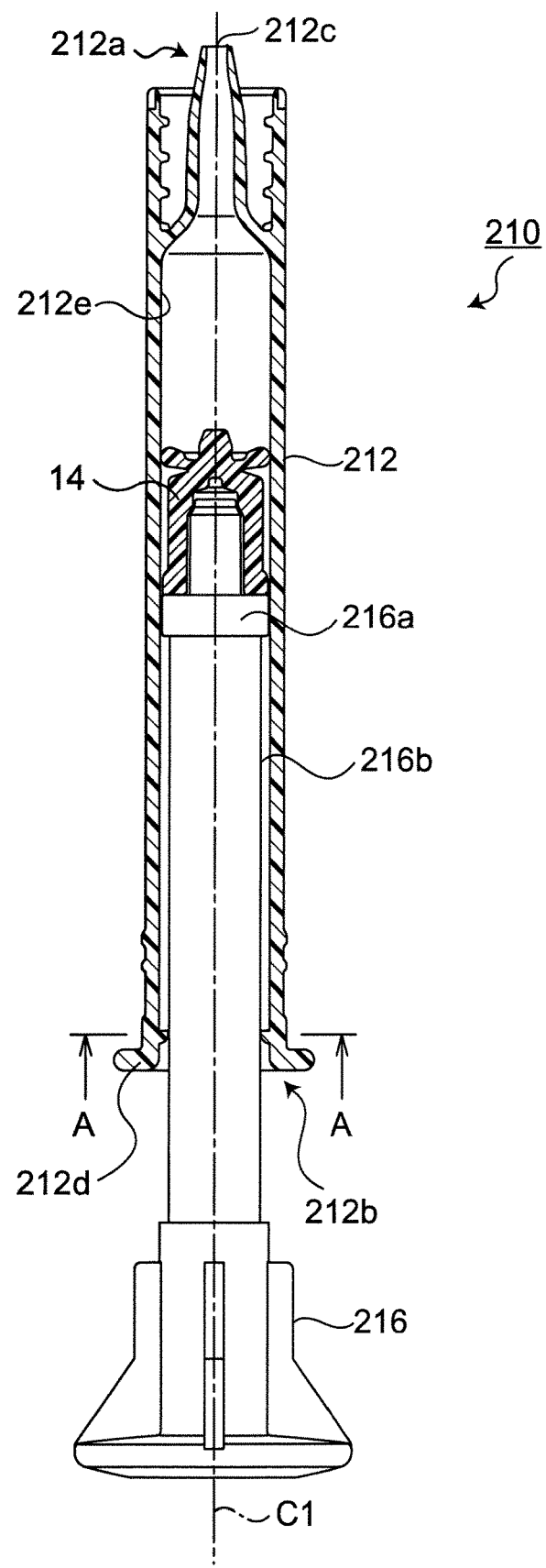
FIG. 11 is a partial cross-sectional view of an injector according to a third embodiment of the present invention.
Figure 12:
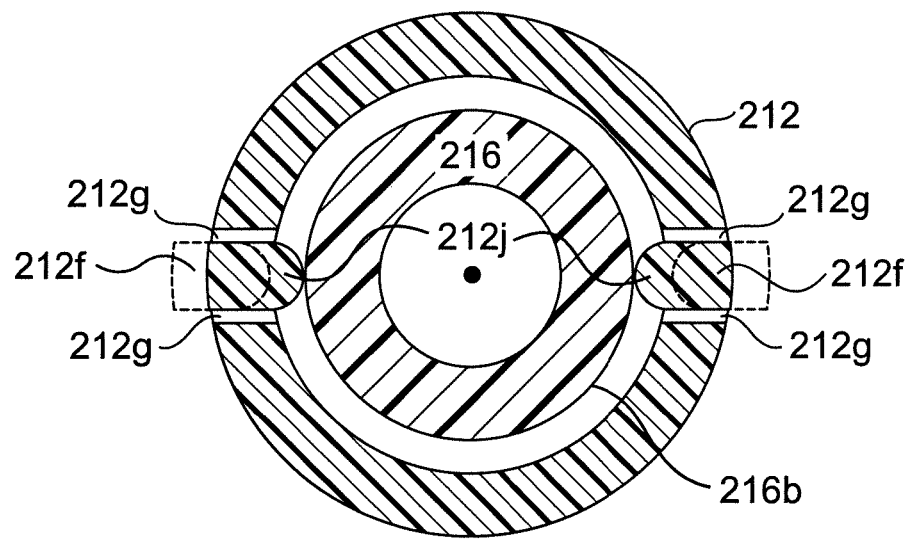
FIG. 12 is a cross-sectional view of the injector taken along a line A-A shown in FIG. 11.
Figure 13:
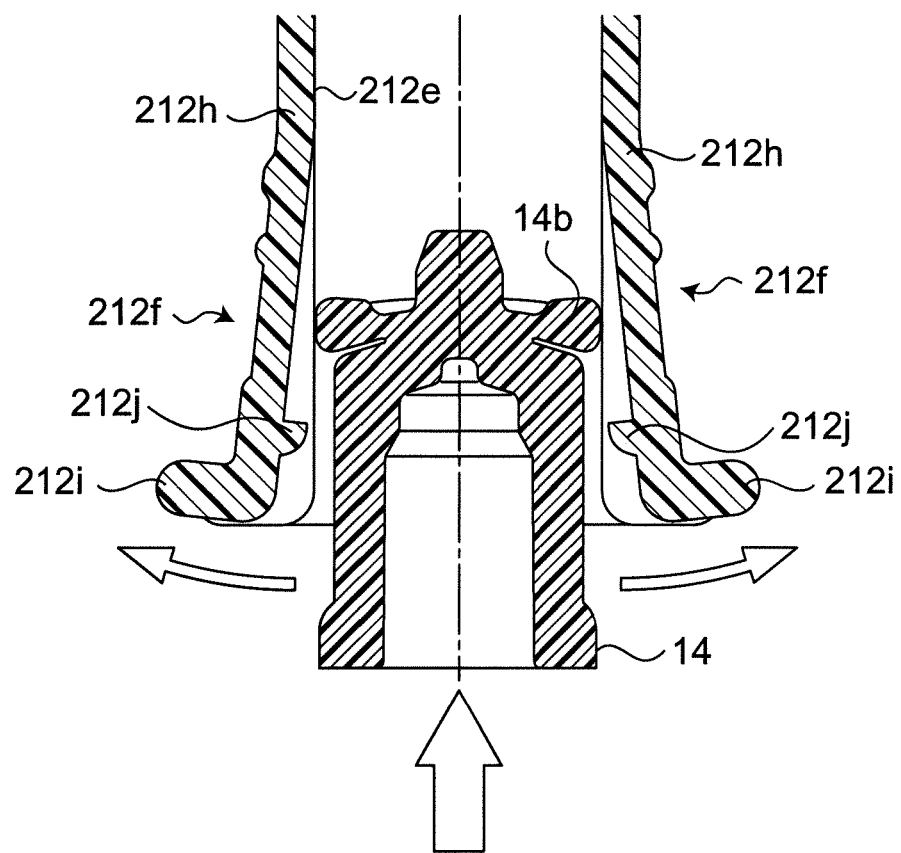
FIG. 13 is an enlarged cross-sectional view of a barrel, showing stoppers when the movable body is housed in the barrel.

FIG. 11 is a partial cross-sectional view of an injector according to the third embodiment. FIG. 12 is a cross-sectional view of the injector taken along a line A-A shown in FIG. 11. FIG. 13 is an enlarged cross-sectional view of a barrel, showing stoppers when the movable body is housed into the barrel. In FIG. 11, the nozzle tip and the finger grip are not shown.

As shown in FIGS. 11 and 12, in an injector 210 according to the third embodiment, no stopper is disposed on a plunger 216. Instead, as shown in FIG. 12, a pair of stoppers 212*f* facing each other is disposed on a barrel 212.

Specifically, in the case of the third embodiment, the stoppers 212*f* are made up of portions of the barrel 212 each interposed between two slits 212*g* formed to extend from a base end 212*b* of the barrel 212. As a result, a portion of the barrel 212 interposed between base portions of the two slits 212*g* is defined as a fixed end 212*h* of the stopper 212*f*. A claw 212*j* brought into elastic contact with the plunger 216 is disposed on the inner side of a free end 212*i* of each of the paired stoppers 212*f*. Therefore, the stopper 212*f* is a plate spring-shaped member (a plate spring-shaped member integrated with the barrel 212) having the fixed end 212*h* attached to the barrel 212 and the free end 212*i* brought into elastic contact with the plunger 216 (via the claws 212*j*).

A distance between the claws 212*j* of the pair of the stoppers 212*f* is made smaller than an outer diameter of a shaft portion 216*b* of the plunger 216. As a result, the pair of the claws 212*j* holds the shaft portion 216*b* of the plunger 216. Consequently, the plunger 216 is prevented from coming off from the barrel 212.

The plunger 216 during retraction toward the base end 212*b* of the barrel 212 due to pulling by the user is restrained when a contact portion 216*a* for contact with the movable body 14 is brought into contact with the claws 212*j*. As a result, the plunger 216 is prevented from coming off from the barrel 212.

As shown in FIG. 13, when the movable body 14 is housed into the barrel 212, the pair of the stoppers 212*f* is elastically deformed such that the free ends 212*i* move away from each other. As a result, the movable body 14 can be housed into the barrel 212 without bringing the claws 212*j* of the stoppers 212*f* into contact with the seal body 14*b*.

In the third embodiment as described above, as with the first embodiment, the seal body and the plunger can be brought into separable contact with each other in the injector capable of suppressing the subsequent dripping of the fluid.

Although the present invention has been described with three embodiments, the present invention is not limited to these embodiments.

For example, in the case of the first embodiment, as shown in FIG. 8A, the planar-shaped rear end surface 14*d* of the movable body 14 and the planar-shaped contact surface 16*b* of the plunger 16 come into separable contact with each other. Therefore, the movable body 14 and the plunger 16 are configured to come into plane contact with each other. However, the embodiments of the present invention are not limited thereto. For example, the movable body may include a hemispherical concave portion at the rear end thereof, and the plunger may include a hemispherical convex portion engageable with the concave portion.

In the case of the first embodiment described above, as shown in FIG. 6, the movable body 14 has the flange 14*c* disposed at the rear end of the main body 14*a*. The flange may be disposed in a portion of the main body other than the rear end. However, to suppress the tilt of the movable body, the seal body is preferably separated from the flange.

Regarding the flange, at least three projecting portions disposed at regular intervals on the movable body in a circumferential direction of the main body can function as a substitute for the flange. In this case, a distance from the central axis of the movable body to a leading end of at least one of the projecting portions is made smaller than a half of the outer diameter of the seal body.

Therefore, in a broad sense, the injector according to the embodiment of the present invention is an injector comprising a cylindrical barrel, a movable body housed in the barrel, and a plunger coming into separable contact with the movable body, the movable body includes a main body having an outer diameter smaller than an inner diameter of the barrel, a disk-shaped seal body disposed on the main body and including an outer circumferential end brought into close contact with an inner circumferential surface of the barrel, and at least one projecting portion projecting from the main body toward the inner circumferential surface of the barrel, and a distance from a central axis of the movable body to a leading end of the at least one projecting portion is smaller than a half of an outer diameter of the seal body.

INDUSTRIAL APPLICABILITY

The present invention is applicable to any injector for injecting a fluid as long as the injector has a seal body and a plunger brought into separable contact with each other.

EXPLANATIONS OF LETTERS OR NUMERALS 10 injector
12 barrel
12*e* inner circumferential surface

14 movable body
14*a* main body
14*b* seal body
14*c* at least one projecting portion (flange)
16 plunger

What is claimed is:

1. An injector comprising:
   a cylindrical barrel;
   a movable body housed in the barrel; and
   a plunger coming into separable contact with the movable body, wherein the movable body includes:
   a main body having an outer diameter smaller than an inner diameter of the barrel,
   a disk-shaped seal body disposed on the main body and including an outer circumferential end brought into close contact with an inner circumferential surface of the barrel in a fluid-tight manner to prevent a movement of fluid between the outer circumferential end of the disk-shaped seal body and the inner circumferential surface of the barrel in a first direction, the first direction extending from a discharge port at a leading end of the barrel to a base end opposite to the leading end, and to prevent a movement of fluid in a second direction opposite to the first direction, and
   at least one projecting portion projecting from the main body toward the inner circumferential surface of the barrel,
   wherein a distance from a central axis of the movable body to a leading end of the at least one projecting portion is smaller than a half of an outer diameter of the seal body,
   wherein the plunger includes a planar-shaped contact surface at a front end thereof, and the movable body includes a planar-shaped rear end surface coming into contact with the contact surface of the plunger,
   wherein the plunger includes a guide pin projecting from the contact surface, and the movable body includes in the rear end surface a guide hole receiving the guide pin,
   wherein an outer diameter of the guide pin is smaller than an inner diameter of the guide hole so that the guide pin enters into and exits from the guide hole of the movable body housed in the barrel,
   wherein the disk-shaped seal body has a central portion attached to an axial front end of the main body, and an outer circumferential side portion that is spaced apart from the axial front end of the main body by an axial gap,
   wherein the at least one projecting portion is a flange, and an outer diameter of the flange is smaller than the outer diameter of the seal body, and
   wherein a distance between the seal body and the flange is larger than the outer diameter of the seal body.

2. The injector according to claim 1, wherein the outer diameter of the flange is smaller than the inner diameter of the barrel.

3. The injector according to claim 1, wherein the outer circumferential side portion is configured to be elastically deformed so as to decrease the axial gap between the outer circumferential side portion and the axial front end of the main body during movement of the moveable body, and such that the axial gap is restored when the movement is stopped.

* * * * *